United States Patent
Rizkalla et al.

(10) Patent No.: US 10,669,247 B2
(45) Date of Patent: Jun. 2, 2020

(54) CARRIER TREATMENT TO IMPROVE CATALYTIC PERFORMANCE OF AN ETHYLENE OXIDE CATALYST

(71) Applicant: Scientific Design Company, Inc., Little Ferry, NJ (US)

(72) Inventors: Nabil Rizkalla, Rivervale, NJ (US); Andrzej Rokicki, Mountain Lakes, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 15/700,813

(22) Filed: Sep. 11, 2017

(65) Prior Publication Data

US 2017/0369460 A1 Dec. 28, 2017

Related U.S. Application Data

(62) Division of application No. 14/811,309, filed on Jul. 28, 2015, now Pat. No. 9,758,498, which is a division of application No. 14/279,534, filed on May 16, 2014, now Pat. No. 9,095,843.

(60) Provisional application No. 61/824,108, filed on May 16, 2013.

(51) Int. Cl.
| | |
|---|---|
| *C07D 301/10* | (2006.01) |
| *C01F 7/02* | (2006.01) |
| *B01J 23/50* | (2006.01) |
| *B01J 23/66* | (2006.01) |
| *B01J 23/68* | (2006.01) |
| *B01J 21/04* | (2006.01) |
| *B01J 37/06* | (2006.01) |
| *B01J 37/02* | (2006.01) |

(52) U.S. Cl.
CPC ............ *C07D 301/10* (2013.01); *B01J 21/04* (2013.01); *B01J 23/50* (2013.01); *B01J 23/66* (2013.01); *B01J 23/688* (2013.01); *B01J 37/0201* (2013.01); *B01J 37/0207* (2013.01); *B01J 37/06* (2013.01); *C01F 7/02* (2013.01)

(58) Field of Classification Search
CPC . C07D 301/10; C01F 7/02; B01J 23/50; B01J 23/66; B01J 23/68; B01J 21/04; B01J 37/06; B01J 37/02
See application file for complete search history.

(56) References Cited

U.S. PATENT DOCUMENTS

| | | | |
|---|---|---|---|
| 2,901,441 A | 8/1959 | Waterman | |
| 3,563,914 A | 2/1971 | Wattimena | |
| 3,702,259 A | 11/1972 | Nielsen | |
| 3,957,690 A | 5/1976 | Bobolev et al. | |
| 4,740,493 A | 4/1988 | Boehning | |
| 4,761,394 A | 8/1988 | Lauritzen | |
| 4,766,105 A | 8/1988 | Lauritzen | |
| 4,797,172 A | 1/1989 | Alvarado Cendan et al. | |
| 4,797,270 A | 1/1989 | Alvarado et al. | |
| 4,908,343 A | 3/1990 | Bhasin | |
| 4,994,587 A | 2/1991 | Notermann et al. | |
| 5,011,807 A | 4/1991 | Hayden et al. | |
| 5,057,481 A | 10/1991 | Bhasin | |
| 5,099,041 A | 3/1992 | Hayden et al. | |
| 5,102,848 A | 4/1992 | Soo et al. | |
| 5,112,795 A | 5/1992 | Minahan et al. | |
| 5,187,140 A | 2/1993 | Thorsteinson et al. | |
| 5,407,888 A | 4/1995 | Herzog et al. | |
| 5,504,053 A | 4/1996 | Chou et al. | |
| 6,103,916 A | 8/2000 | Takada et al. | |
| 6,368,998 B1 | 4/2002 | Lockemeyer | |
| 6,579,825 B2 | 6/2003 | Lockemeyer | |
| 6,656,874 B2 | 12/2003 | Lockemeyer | |
| 6,750,173 B2 | 6/2004 | Rizkalla et al. | |
| 6,846,774 B2 | 1/2005 | Rizkalla | |
| 7,439,375 B2 | 10/2008 | Lockemeyer | |
| 7,932,407 B2 | 4/2011 | Matusz et al. | |
| 7,951,748 B2 | 5/2011 | Lu et al. | |
| 8,895,469 B2 * | 11/2014 | Chen | B01J 21/04 502/100 |
| 9,073,035 B2 * | 7/2015 | Richard | C07D 301/10 |
| 9,339,798 B2 * | 5/2016 | Richard | C07D 301/10 |
| 2003/0191019 A1 | 10/2003 | Rizkalla et al. | |

(Continued)

FOREIGN PATENT DOCUMENTS

| | | | |
|---|---|---|---|
| CA | 2343836 A1 * | 3/2000 | ............. B01J 23/66 |
| CN | 1167500 A | 12/1997 | |

(Continued)

OTHER PUBLICATIONS

CN1317992—family, 2020, printout of complete family of patents for CN 1317992.*
English-language translation of the Taiwanese Office Action dated Sep. 29, 2017, received in a corresponding foreign application.
Drake, L.C., et al., "Macropore-Size Distributions in Some Typical Porous Substances", Ind. Eng. Chem. Anal. Ed., Publication Date: Dec. 1945, 17 (12), pp. 787-791.
Brunauer, S., et al., "Adsorption of Gases in Multimolecular Layers", J. Am. Chem. Soc., Feb. 1938, pp. 309-316.

(Continued)

*Primary Examiner* — Sun Jae Yoo
(74) *Attorney, Agent, or Firm* — Scully Scott Murphy and Presser

(57) ABSTRACT

A method for lowering the sodium content of different carriers which may have different physical properties as well as varying degrees of sodium is provided. The method, which lowers the sodium content from the surface, subsurface as well as the binding layer of the carrier, includes contacting a carrier with water. A rinse solution is recovered from the contacting. The rinse solution includes leached sodium from the carrier. The sodium content in the rinse solution is then determined. The contacting, recovering and determining are repeated until a steady state in the sodium content is achieved.

17 Claims, 3 Drawing Sheets

(56) References Cited

U.S. PATENT DOCUMENTS

| | | | |
|---|---|---|---|
| 2005/0085649 | A1 | 4/2005 | Lockemeyer |
| 2005/0101790 | A1 | 5/2005 | Rizkalla et al. |
| 2007/0100151 | A1 | 5/2007 | Lu et al. |
| 2009/0177000 | A1* | 7/2009 | Natal ............... B01J 21/04 549/534 |
| 2010/0280261 | A1 | 10/2010 | Howard et al. |
| 2012/0022277 | A1 | 1/2012 | Hashimoto et al. |
| 2012/0108832 | A1 | 5/2012 | Chen et al. |
| 2012/0264953 | A1 | 10/2012 | Rosendahl et al. |

FOREIGN PATENT DOCUMENTS

| | | |
|---|---|---|
| CN | 1317992 A | 10/2001 |
| CN | 101272853 A | 9/2008 |
| CN | 102463141 A1 | 5/2012 |
| DE | 2933950 A1 | 3/1981 |
| TW | 200523018 A | 7/2005 |
| TW | 200803979 A | 1/2008 |
| WO | 96/36563 | 11/1996 |

OTHER PUBLICATIONS

Hoflund, G. B., et al., "Study of CS-promoted α-alumina-supported silver, ethylene epoxidation catalysts" Journal of Catalysis, Aug. 1996, pp. 48-53, vol. 162, Issue 1.
Hoflund, G. B., et al., "Ion-beam characterization of alumina-supported silver catalysts used for ethylene epoxidation", Nuclear Instruments and Methods in Physics Research Section B: Beam Interactions with Materials and Atoms Section B, Sep. 1996, pp. 517-521 vol. 118, Issue 1-4.
International Search Report and Written Opinion dated Feb. 4, 2015 from related International Application No. PCT/US2014/038020.
Chinese Office Action dated Oct. 27, 2016 received in a corresponding foreign application and an English-language translation thereof.
Chinese Office Action dated Aug. 16, 2016 received in Chinese Patent Application No. CN 201480028398.8 together with an English language translation.
Chinese Office Action dated Mar. 27, 2017 received in Chinese Patent Application No. CN 201480028398.8 together with an English language translation.
Chinese Office Action dated Aug. 21, 2017 received in Chinese Patent Application No. CN 201480028398.8 together with an English language translation.
Chinese Office Action dated Sep. 27, 2018 received in Chinese Patent Application No. CN 201480028398.8 together with an English language translation.
Extended European Search Report dated Dec. 6, 2016 received in European Patent Application No. EP 14797291.3.
European Office Action dated Oct. 24, 2018 received in European Patent Application No. EP 14797291.3.
Third Party Observation dated Feb. 11, 2017 received in European Patent Application No. EP 20140797291.
Gulf Cooperation Council Examination Report dated Apr. 18, 2017 received in Gulf Cooperation Council Patent Application No. GC 2014-27173.
Gulf Cooperation Council Examination Report dated Jul. 20, 2017 received in Gulf Cooperation Council Patent Application No. GC 2014-27173.
Indian Office Action dated Dec. 17, 2018 received in Indian patent Application No. IN 10321/DELNP/2015.
Taiwan Office Action dated Oct. 20, 2017 received in Taiwan Patent Application No. TW 103116834 together with an English language translation.
Carvalho, M. et al., "The promoting effect of cesium on structure and morphology of silver catalysts", Annals of the Brazilian Academy of Sciences, 2004, pp. 19-27, vol. 76, No. 1.
Karavasilis, C. et al., "In Situ Controlled Promotion of Catalyst Surfaces via NEMCA: The Effect of Na on the Ag-Catalyzed Ethylene Epoxidation in the Presence of Chlorine Moderators", Journal of Catalysis, 1996, pp. 205-213, vol. 160.
International Search Report and Written Opinion dated Feb. 4, 2015 received in International Application No. PCT/US2014/038022.
Notification of Reexamination dated Nov. 19, 2019 received in Chinese Patent Application No. 201480028228.X together with an English language translation.
Office Action dated Dec. 13, 2019 received in European Patent Application No. 14 797 166.7.
Search Report dated Feb. 4, 2020 received from the Brazilian Patent Office in related application BR 112015028724-7 together with an English language translation.

* cited by examiner

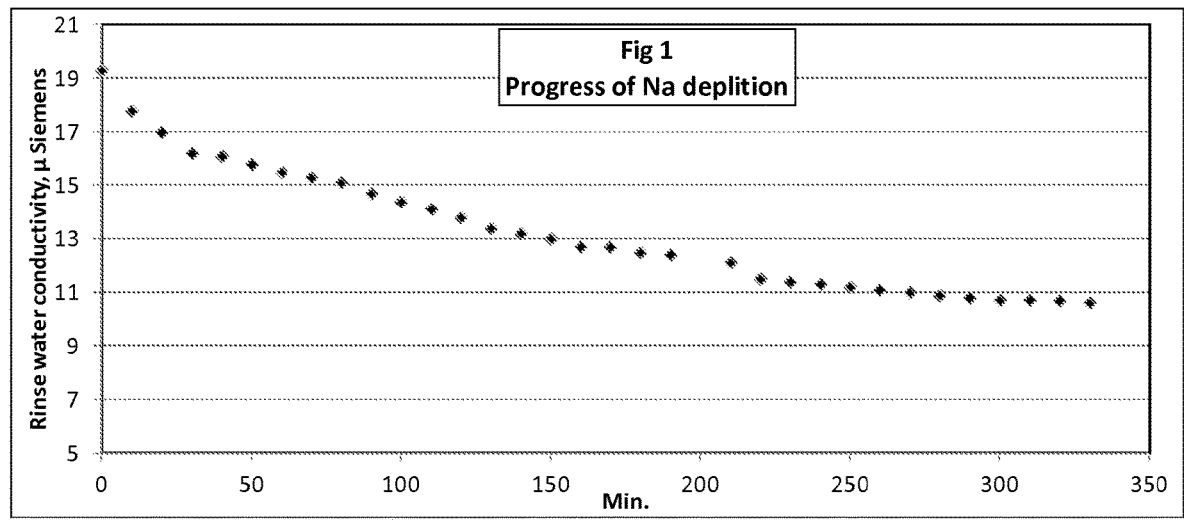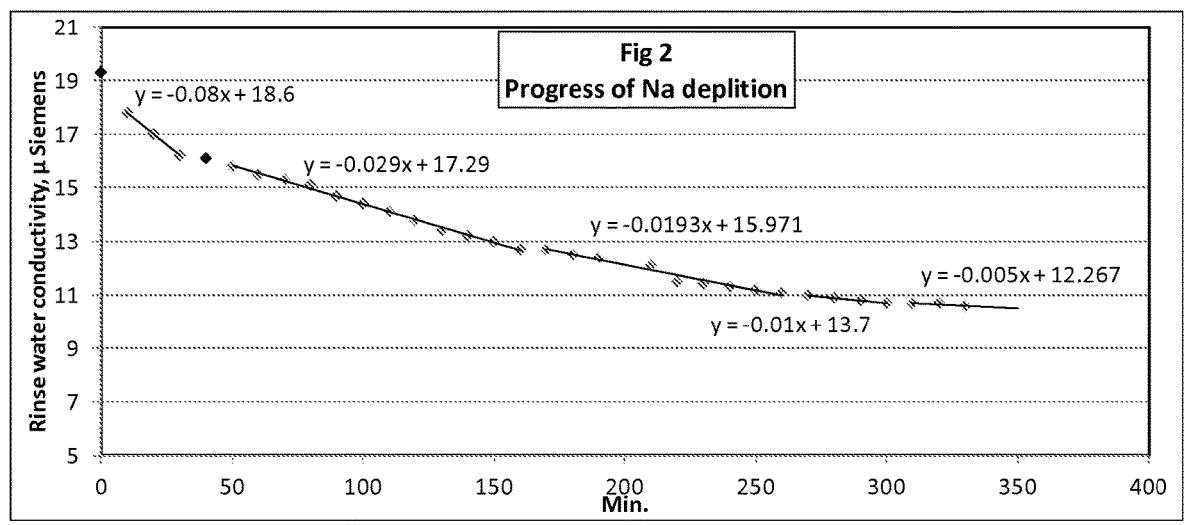

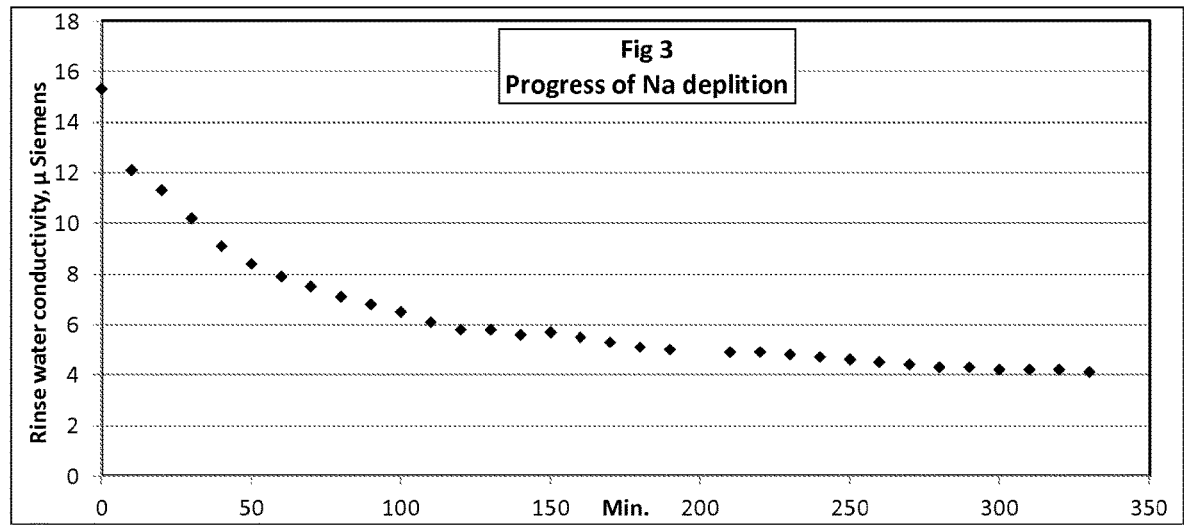
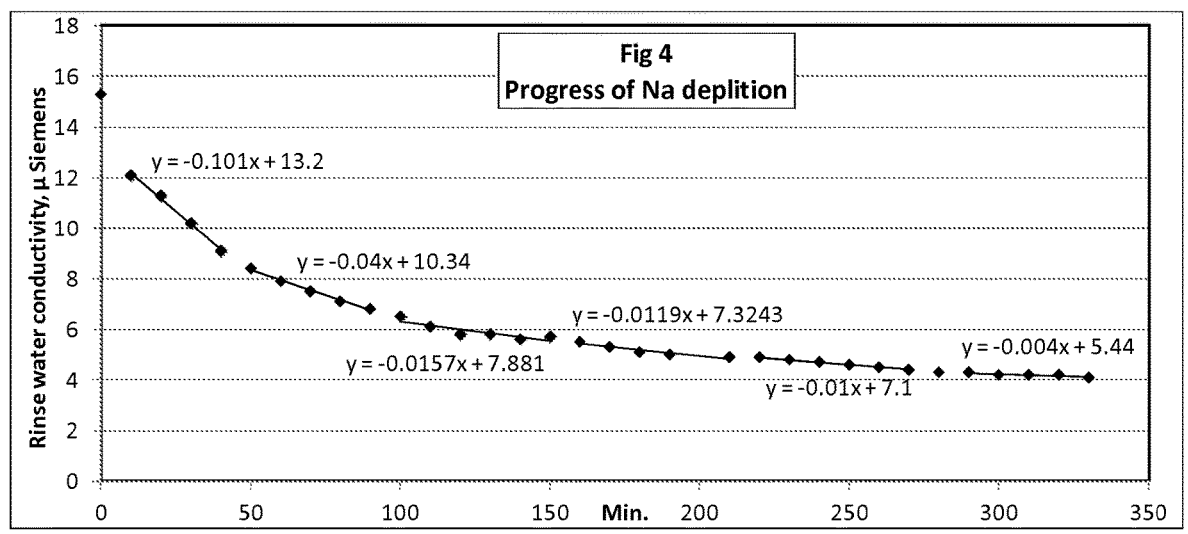

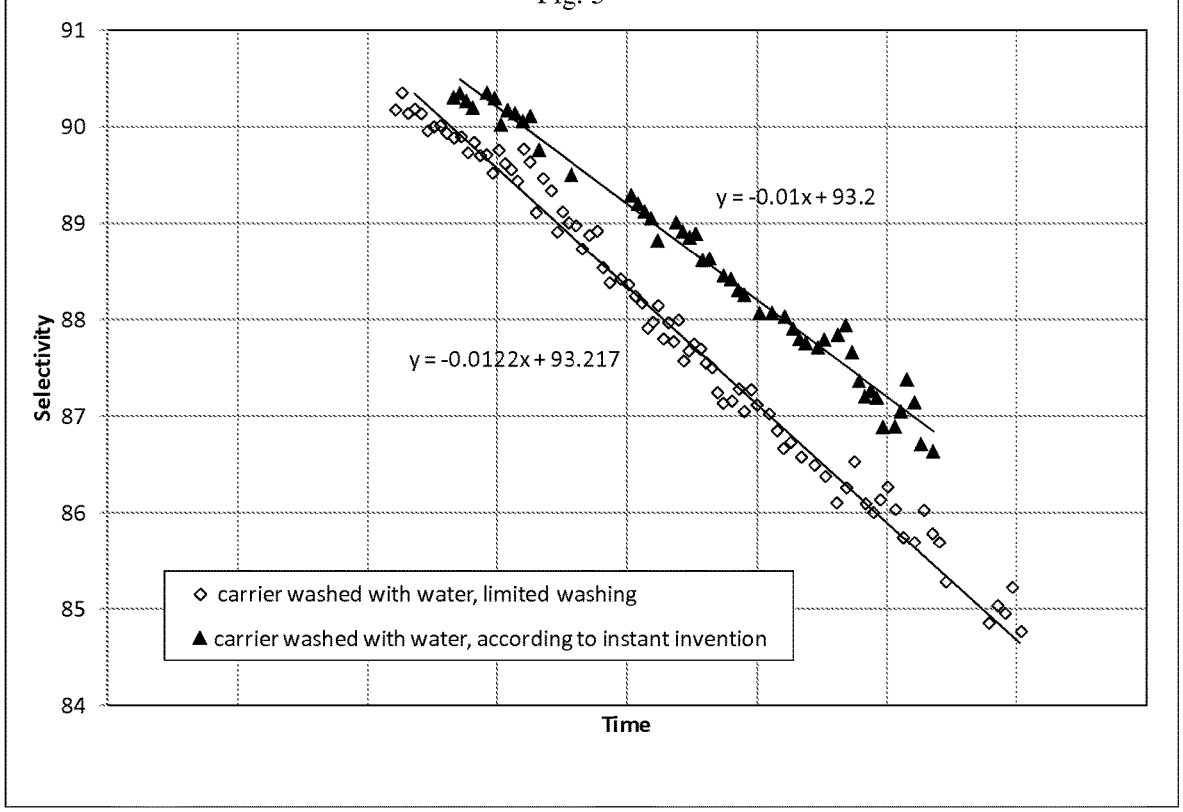

CARRIER TREATMENT TO IMPROVE CATALYTIC PERFORMANCE OF AN ETHYLENE OXIDE CATALYST

CROSS REFERENCE TO RELATED APPLICATION

This application is a divisional of U.S. patent application Ser. No. 14/811,309, filed Jul. 28, 2015, which is a divisional of U.S. patent application Ser. No. 14/279,534, filed May 16, 2014, now U.S. Pat. No. 9,095,843, which claims the benefit of U.S. Provisional Patent Application No. 61/824,108 filed May 16, 2013, the entire content and disclosure of each is incorporated herein by reference.

FIELD OF THE DISCLOSURE

The present disclosure relates to improved carriers for a silver-based ethylene oxide catalyst, and more particularly, to a carrier treatment process which lowers the sodium content of the carrier. The present disclosure also relates to a silver-based ethylene oxide catalyst that includes such a carrier and a process of producing ethylene oxide using the silver-based ethylene oxide catalyst.

BACKGROUND

As known in the art, high selectivity catalysts (HSCs) for the epoxidation of ethylene refer to those catalysts that possess selectivity values higher than high activity catalysts (HACs) used for the same purpose. Both types of catalysts include silver as the active catalytic component on a refractory support (i.e., carrier). Typically, one or more promoters are included in the catalyst to improve or adjust properties of the catalyst, such as selectivity.

Generally, but not necessarily always, HSCs achieve the higher selectivity (typically 87 mole % or above) by incorporation of rhenium, and or an oxyanion of tungsten, molybdenum, or chromium as promoters. Typically, one or more additional promoters selected from alkali metals (e.g., lithium, potassium, and/or cesium), alkaline earth metals, transition metals (e.g., tungsten compounds), and main group metals (e.g., sulfur and/or halide compounds) are also included.

There are also ethylene epoxidation catalysts that may not possess the selectivity values typically associated with HSCs, though the selectivity values are improved over HACs. These types of catalysts can also be considered within the class of HSCs, or alternatively, such catalysts can be considered to belong to a separate class, e.g., "medium selectivity catalysts" or "MSCs." These types of catalysts typically exhibit selectivities of at least 83 mole % and up to 87 mole %.

In contrast to HSCs and MSCs, the HACs are ethylene epoxidation catalysts that generally do not include rhenium, and do not provide the selectivity values of HSCs or MSCs. Typically, HACs include cesium (Cs) as the main promoter.

It is well known that with extended use of a catalyst, the catalyst will show signs of ageing (i.e., degraded performance) to a point until use of the catalyst is no longer practical. For obvious reasons, there is a continuous effort to extend the useful lifetime (i.e., "longevity" or "usable life") of the catalyst. The useful lifetime of the catalyst is directly dependent on the stability of the catalyst. As used herein, the "useful lifetime" is the time period for which a catalyst can be used until one or more of its functional parameters, such as selectivity or activity, degrade to such a level that use of the catalyst becomes impractical.

Stability of the catalyst has largely been attributed, in part, to various characteristics of the carrier. Some characteristics of the carrier that have undergone much research include carrier formulation, surface area, porosity, particle morphology, and pore volume distribution, among others.

The most widely used formulation for the carriers of ethylene epoxidation catalysts are those based on alumina, typically $\alpha$-alumina. Much research has been directed to investigating the effect of the alumina composition for improving stability and other properties of the catalyst.

For example, the presence of sodium (Na) in an $\alpha$-alumina carrier plays an important role in the ageing of an ethylene oxide catalyst. This fact was recognized for some time and several publications show evidence that confirmed the degrading effect of Na present on the surface of the carrier. For instance, ISS analysis showed the increase of Na and chloride (Cl) on the surface as the catalyst ages. XPS data showed that the binding energy of both surface Na and Cl correspond to the formation of NaCl on the surface of the aged catalyst, Cl is adsorbed from the gas feed. See, for example, the publications to G. Hoflund and D. Minahan entitled "Study of Cs-promoted $\alpha$-alumina-supported silver, ethylene epoxidation catalysts" Journal of Catalysis, 162, 1996, 48 and "Ion-beam characterization of alumina-supported silver catalysts used for ethylene epoxidation" Nuclear Instruments and Methods in Physics Research Section B: Beam Interactions with Materials and Atoms, 118, Issues 1-4, 1996, 517. It was suggested in the aforementioned publications that Na migrates from the binder to the surface is accelerated by the driving potential provided by the surface chloride.

There are many publications which describe $\alpha$-alumina carrier treatment processes that are aimed at improving the catalytic performance, e.g., stability of the resultant catalyst that is formed on the treated carrier. The processes generally wash the carrier prior to impregnating the carrier with silver and other promoters. The prior art treatment processes are limited in scope in carrier treatments that deal generally with removing Na from the surface of the carrier. For instance, both U.S. Pat. Nos. 2,901,441 and 3,957,690 disclose a procedure for washing a carrier of a silver catalyst. In these publications, the $\alpha$-alumina carrier is washed by heating in a hot aqueous solution of organic acid and then rinsed with water. U.S. Pat. Nos. 5,102,848 and 5,504,053 disclose washing of an $\alpha$-alumina carrier using hot water. Similarly, U.S. Pat. No. 6,103,916 discloses washing of an $\alpha$-alumina carrier for an ethylene oxidation catalyst. In the '916 publication, washing is aimed to remove "leachable Na". To test the carrier for its leachable Na, the washed carrier is boiled in water and the resistivity of the drained water is more than 10,000$\Omega$. Also, U.S. Pat. Nos. 6,368,998, 6,579,825, 6,656,874, and 7,439,375 disclose a process of lowering a concentration of ionizable species present on the surface of the carrier. The ionizable species, especially silicates, were extracted by boiling in deionized water. The process was repeated 3 times for 15 minutes, each.

By contrast, DE2933950 shows experimental evidence that soluble alkali metal silicates are responsible for degrading the catalytic performance. The EP '950 publication discloses a process of washing the carrier with a hot NaOH solution to remove these salts and improve the catalytic performance. Also, U.S. Pat. No. 6,846,774 discloses washing the alumina carrier, of an ethylene oxide catalyst, with a hot aqueous basic solution and maintaining the pH of the solution above 8.

Despite the numerous carrier treatments that are available to remove Na from the surface of a carrier, there remains a need in the art for additional carrier treatment processes which provide further improvements in the stability of an ethylene oxide catalyst. There is a particular need for improving the stability of such catalysts by providing a means to remove Na not only from the surface of the carrier, but from the subsurface and the binding layer of the carrier.

SUMMARY

In one embodiment, the present disclosure provides a means to lower the surface and subsurface sodium content of a carrier as well as the majority of the sodium in the binding layer of the carrier. As such and in the washed carriers of the present disclosure, the migration of sodium ions will be primarily limited to the more stable sodium within the bulk of the carrier. This migration will continue but it is, comparatively, rather slow in nature.

Specifically, the present disclosure provides a method for treating different carriers which may have different physical properties as well as varying degrees of sodium contamination. In the method of the present disclosure, the carrier is rinsed with water. The carrier rinsing continues, or is repeated, even if the concentration of surface sodium drops to a conventionally low level. Actually that drop is intended to be the initial phase of the rinsing process. The Na depleted surface will enhance the potential for faster sodium ion migration from the subsurface of the carrier and from the binder's bulk, for further removal.

The disclosure is different from the prior art by the fact that it recognized that different commercial carriers may contain different levels of surface Na. Therefore, washing the carrier until the Na level reached a certain level is an unreliable strategy. For all carriers, the Na depletion will start with a, relatively, higher level, and with continuous washing the rate of Na depletion will drop. This drop is an indication that the readily available surface Na is being exhausted and the continuous washing is now removing the subsurface Na. The present disclosure teaches that the washing procedure should continue until a steady state of Na depletion is achieved.

The sodium removal efficiency is monitored using conventional methods, e.g., elemental analysis of the rinse solution or via measuring the electrical conductivity of the rinsing solution. Deionized water is not an efficient medium for electrical conductivity. The extracted sodium in the water, as well as the small amount of other dissolved ions, will carry a current and provides a measurable electrical conductivity. The magnitude of this conductivity will be a function of the concentration of sodium. In the treatment process of the present disclosure, the rate of sodium removal continues to drop with each additional cycle of rinsing. This is a sign that the surface sodium is depleted and the slower rate is a function of the slower diffusion of subsurface sodium to the surface. With continual rinsing the sodium level in the rising solution drops and accordingly the conductivity of the rinsing water, also, gradually drops, as a sign of depleted sodium from deeper zones of the carrier subsurface. This process continues until a steady state is achieved, i.e., when the amount of depleting sodium reaches, for all practical purpose, a constant level. This indicates that all the surface and subsurface sodium has been virtually removed and additional treatment is not needed because it will only affect the bulk sodium which is not expected to be totally removed.

The steady state is defined when at least three successive rinsing cycles result in removing the same level of sodium, as measured by analysis, or by the electrical conductivity of the rinsing water. By "same level" is meant that the electrical conductivity of the three, or more, successive rinsing cycles is within a value of ±0.5%.

In another embodiment of the present invention, the steady state can be determined when the slope of the change in conductivity of the rinsing water is lower than $2\mu$ Siemens/hour of treatment, preferably lower than $1\mu$ Siemens per hour of rinsing, and most preferably lower than $0.5\mu$ Siemens/hr of rinsing.

In one aspect of the present disclosure, a method of treating carriers is provided that lowers sodium content of the carrier. The method includes: contacting a carrier with water; recovering a rinse solution from the contacting of the carrier with the water, the rinse solution comprises leached sodium from the carrier; determining sodium content in the rinse solution; and repeating the contacting, recovering and determining until a steady state in the sodium content is achieved. In some embodiments, the sodium content in the rinse solution can be determined by measuring the electrical conductivity of the rinse solution.

In another aspect of the present disclosure, a process for producing an ethylene oxide catalyst useful in the epoxidation of ethylene to ethylene oxide is provided. This process comprises selecting a carrier; contacting the carrier with water; recovering a rinse solution from the contacting of the carrier with the water, the rinse solution comprises leached sodium from the carrier; determining sodium content in the rinse solution, wherein the contacting, recovering and determining are repeated until a steady state in the sodium content is achieved; depositing a catalytic effective amount of silver on the carrier; and depositing a promoting amount of at least one promoter prior to, coincidentally with, or subsequent to the deposition of the catalytic effective amount of silver.

In yet another aspect of the present disclosure, a method for the vapor phase conversion of ethylene to ethylene oxide in the presence of oxygen is provided. This method of the present disclosure comprises reacting a reaction mixture comprising ethylene and oxygen in the presence of a catalyst that is prepared by: selecting a carrier; contacting the carrier with water; recovering a rinse solution from the contacting of the carrier with the water, the rinse solution comprises leached sodium from the carrier; determining sodium content in the rinse, wherein the contacting, recovering and determining are repeated until a steady state in the sodium content is achieved; depositing a catalytic effective amount of silver on said carrier; and depositing a promoting amount of at least one promoter prior to, coincidentally with, or subsequent to the deposition of the catalytic effective amount of silver.

In yet a further aspect of the present disclosure, a carrier for a silver-based ethylene oxide catalyst is provided. The carrier of the present disclosure is characterized as having depleted Na from the surface and near subsurface. A sign of the efficient depletion is when successive water washing of the treated carrier yields, virtually, the same amount of extracted sodium. This constant amount is generally in the 5-20 ppm level, as measured by the residual sodium extraction test. The exact level of the residual sodium will vary, as a function of the carrier composition, the concentration of sodium in the alpha alumina and the binding material and the details of processing the carrier during its manufacturing.

In yet a further aspect of the present disclosure, a silver-based ethylene oxide catalyst is provided. The catalyst of the present disclosure comprises a carrier having a steady state sodium content of 20 ppm or less; a catalytic effective amount of silver; and promoting amount of at least one promoter.

BRIEF DESCRIPTION OF THE DRAWINGS

FIG. 1 is a graph of the rinse water conductivity (μ Siemens/hr) vs. time (minutes, min.) for Carrier C in accordance with Example 3 of the present disclosure.

FIG. 2 is a graph of the rinse water conductivity (μ Siemens/hr) vs. time (minutes, min.) for Carrier C in accordance with Example 3 of the present disclosure.

FIG. 3 is a graph of the rinse water conductivity (μ Siemens/hr) vs. time (minutes, min.) for Carrier C in accordance with Example 4 of the present disclosure.

FIG. 4 is a graph of the rinse water conductivity (μ Siemens/hr) vs. time (minutes, min.) for Carrier C in accordance with Example 4 of the present disclosure.

FIG. 5 is a graph of selectivity vs. time for Catalyst A and Catalyst B that are described in Example 5 of the present disclosure.

DETAILED DESCRIPTION

In one aspect, the present disclosure is directed to an improved carrier for an ethylene epoxidation catalyst. The carrier is improved in that it imparts an enhanced stability to a silver-based catalyst derived therefrom. By 'enhanced stability' it is meant that the silver-based catalysts supported on the carrier of the present disclosure have longer usable lifetimes, and particularly, a significantly reduced degradation in selectivity as compared to such catalysts, impregnated on a prior art carrier over equivalent time periods of usage.

The improved carrier is achieved by lowering the surface and subsurface sodium content of a carrier as well as the sodium content in the binding layer. This lowering is achieved using successive rinsing with water at a defined temperature until a steady state in sodium content is achieved.

The carrier that can be employed in the present disclosure may be selected from a large number of solid supports which may be porous or nonporous. The carriers are relatively inert to the epoxidation feedstock materials, products and reaction conditions for the intended use, such as for the epoxidation of an olefin. The carrier that can be employed may be a refractory inorganic material such as, for example, alumina-, silica- or titania-based compounds, or combinations thereof such as alumina-silica carriers.

In one embodiment, the carrier is an alumina carrier. The alumina carrier that can be employed in the present disclosure is composed of any of the refractory alumina compositions known in the art for use in ethylene oxidation catalysts. In one embodiment of the present disclosure, the carrier that is employed includes alpha-alumina as the alumina component. The alpha-alumina used in the present disclosure typically has a high purity, i.e., about 80 weight % or more, and more typically, 95 weight % or more alpha-alumina. Remaining components of the alumina carrier of the present disclosure may be other phases of alumina, silica, mullite, alkali metal oxides and trace amounts of other metal-containing and/or non-metal-containing additives or impurities.

When an alumina carrier is employed, the alumina carrier is typically porous and, in one embodiment, has a B.E.T. surface area of at most 20 m$^2$/g. In another embodiment, the B.E.T. surface area of the alumina carrier is in the range from 0.1 m$^2$/g to 10 m$^2$/g. In yet another embodiment of the present disclosure, the alumina carrier that can be employed in the present disclosure has a B.E.T. surface area from 0.2 m$^2$/g to 3 m$^2$/g. In a further embodiment, the alumina carrier that can be employed in the present disclosure is characterized by having a B.E.T. surface area from 0.3 m$^2$/g to 3 m$^2$/g, preferably from 0.5 m$^2$/g to 2.5 m$^2$/g, and more preferably from 0.6 m$^2$/g to 2.0 m$^2$/g. The B.E.T. surface area described herein can be measured by any suitable method, but is more preferably obtained by the method described in Brunauer, S., et al., *J. Am. Chem. Soc.*, 60, 309-16 (1938).

In one embodiment, the alumina carrier that can be employed in the present disclosure has a water absorption value ranging from 0.2 cc/g to 0.8 cc/g. In another embodiment, the alumina carrier that can be employed in the present disclosure has a water absorption value ranging from 0.25 cc/g to 0.6 cc/g.

The alumina carrier that can be employed in the present disclosure can have any suitable distribution of pore diameters. As used herein, the "pore diameter" is used interchangeably with "pore size". In one embodiment, the pore diameters are at least 0.01 microns (0.01 μm). In another embodiment, the pore diameters are at least 0.1 μm. In different embodiments, the pore diameters can be at least 0.2 μm, or 0.3 μm. Typically, the pore diameters are no more than 50 μM.

The alumina carrier that can be employed in the present disclosure can be monomodal or multimodal such as, for example, bimodal. Without wishing to be bound by any theory, it is believed that a catalyst with a bimodal pore size distribution possesses a type of pore structure in which reaction chambers are separated by diffusion channels.

In one embodiment, at least 40% of the pore volume is attributable to pores with diameters between 1 micrometer and 5 micrometers. In another embodiment, at least 60% of the pore volume is attributable to pores with diameters between 1 micrometer and 5 micrometers. In yet a further embodiment, at least 80% of the pore volume is attributable to pores with diameters between 1 micrometer and 5 micrometers.

In one embodiment, the median pore diameter of the carrier employed is between 1 micrometer and 5 micrometers. In another embodiment, the median pore diameter of the carrier employed is between 1 micrometer and 4.5 micrometers. In yet another embodiment, the median pore diameter of the carrier employed is between 1 micrometer and 4 micrometers. The pore volume from pores with a diameter of 5 micrometers and above is typically less than 0.20 ml/g, more typically less than 0.10 ml/g, and even more typically less than 0.05 ml/g. The pore volume from pores with a diameter of 1 micrometer and less is typically less than 0.20 ml/g, and more typically less than 0.16 ml/g.

In some embodiments, the water pore volume of the alumina carrier can be from 0.10 cc/g to 0.80 cc/g. In other embodiments, the water pore volume of the alumina carrier can be from 0.20 cc/g to 0.60 cc/g. The pore volume and pore size distribution of the carrier described herein can be measured by any suitable method, but are more preferably obtained by the conventional mercury porosimeter method as described in, for example, Drake and Ritter, "Ind. Eng. Chem. Anal. Ed.," 17, 787 (1945).

The carrier that can be employed in the present disclosure is prepared utilizing procedures well known in the art. Alternatively, the carrier that can be employed in the present disclosure is commercially available. For example, suitable alumina carriers are manufactured and generally commercially available from Noritake of Nagoya, Japan, and the NorPro Company of Akron, Ohio.

In one embodiment and for example, an alumina carrier can be made by mixing a high-purity aluminum oxide, such as, for example, alpha-alumina, with temporary and permanent binders. The temporary binders, that include burnout materials, are thermally decomposable organic compounds of moderate to high molecular weight which, on decomposition, enhance the pore structure of the carrier. The temporary binders are essentially removed during firing when producing the final carrier. Some examples of burnout materials include cellulose, substituted celluloses, e.g., methylcellulose, ethylcellulose, and carboxyethylcellulose, stearates (e.g., organic stearate esters, such as methyl or ethyl stearate), waxes, granulated polyolefins (e.g., polyethylene and polypropylene), walnut shell flour, and the like, which are decomposable at the firing temperatures used in preparation of an alumina carrier.

The permanent binders are typically inorganic clay-type materials having fusion temperatures below that of the alumina, such as silica, aluminum, calcium or magnesium silicates with one or more alkali metal compounds. Optionally a transitional alumina can be present. The permanent binders typically impart mechanical strength to the finished carrier.

After thorough dry-mixing, sufficient water and/or other suitable liquid is added to help form the mass into a paste-like substance. Carrier particles are formed from the paste by conventional means, such as extrusion. After molding into the desired shape, the carrier particles can be calcined at a temperature from 1200° C. to 1600° C. to form the support. When the particles are formed by extrusion, it may be desirable to also include extrusion aids. The amounts of extrusion aids required depend on a number of factors that relate to the equipment used. Such factors are well within the general knowledge of a person skilled in the art of extruding ceramic materials.

The carrier that can be employed in the present disclosure can be of any suitable shape or morphology. For example, the carrier can be in the form of particles, chunks, pellets, rings, spheres, three-holes, wagon wheels, cross-partitioned hollow cylinders, and the like, of a size preferably suitable for employment in fixed bed reactors. In one embodiment, the carrier particles typically have equivalent diameters in the range of from 3 mm to 12 mm, and more typically in the range of from 5 mm to 10 mm, which are usually compatible with the internal diameter of the tubular reactors in which the catalyst is placed. As known in the art, the term "equivalent diameter" is used to express the size of an irregularly-shaped object by expressing the size of the object in terms of the diameter of a sphere having the same volume as the irregularly-shaped object.

In some embodiments of the present disclosure, and prior to performing the treatment step that lowers the surface and subsurface sodium content of the carrier, the carrier can be treated by contacting or soaking the carrier in a solution of an organic acid, an inorganic acid, a base, a salt, or combinations thereof. In one embodiment, a useful treatment is conducted by contacting or soaking the carrier in a solution of an alkali hydroxide such as sodium hydroxide, potassium hydroxide, or an acid such as $HNO_3$. In one embodiment, the treating is conducted by contacting or soaking the carrier in an aqueous solution of an alkali hydroxide, or $HNO_3$ at a concentration in the range of from 0.01 molar to 10 molar. In another embodiment, the treating is conducted by contacting or soaking the carrier in an aqueous solution of an alkali hydroxide, or $HNO_3$ at a concentration in the range of from 0.05 molar to 5 molar. Useful contacting or soaking times typically range from 1 minute to 30 days, with from 1 minute to 5 days being more typical, and with from 1 minute to 1 day being even more typical. Useful solution temperatures typically range from 0° C. to 250° C., with from 10° C. to 200° C. being more typically, and with from 20° C. to 150° C. being even more typical. After contacting or soaking, the support can be optionally dried by heating at a temperature from 80° C. to 500° C. Contacting or soaking can be done at static conditions or with solution circulation. The treatment optionally may include contacting or soaking at one temperature, usually higher, followed by contacting or soaking at different temperature, usually lower. In one embodiment, the carrier is contacted with sodium hydroxide prior to performing the treatment of the present disclosure that lowers the surface and subsurface Na content of the carrier.

The carrier that can be employed in the present disclosure typically contains a measurable level of sodium on the surface thereof. The concentration of sodium at the surface of the carrier will vary depending on the level of sodium within the different components of the carrier as well as the details of its calcination. In one embodiment of the present disclosure, the carrier that can be employed in the present disclosure has a surface sodium content of from 5 ppm to 200 ppm, relative to the total mass of the carrier. In another embodiment of the present disclosure, the carrier that can be employed in the present disclosure has a surface sodium content of from 7 ppm to 70 ppm, relative to the total mass of the carrier. The sodium content mentioned above represents that which is found at the surface of the carrier and that which can be leached, i.e., removed, by water.

The surface sodium content of the carrier can be determined utilizing a water leachable test. In this test, the carrier is boiled in deionized water for 30 minutes. The ratio of water to carrier is typically 10:1 by weight. At the end of boiling process, the water is analyzed by Inductive Coupled Plasma (ICP). The determined amount of Na is expressed in ppm relative to the total mass of the carrier sample.

Sodium will also be present in the subsurface of the carrier as well as in the bulk. By "subsurface" it is meant the portion of the carrier that is positioned between the surface of the carrier and the bulk of the carrier. Typically, the subsurface of the carrier is located a distance of at most 100 nanometer inward from the surface of the carrier. By "bulk" it is meant the remaining portion of the carrier that is beneath the subsurface of the carrier.

Sodium will also be present in the binding layer as well. The term "binding layer" denotes a layer of binding material that holds the alumina particles in place. In general, the binding layer will be localized between the grain boundaries of the alpha alumina particles. In some embodiments, the binding layer may, partially, cover the surface of the carrier.

A treatment in accordance with the present disclosure is now performed on the carrier. Unlike prior art treatments that reduce the level of surface sodium from a carrier, the treatment of the present disclosure not only lowers the surface sodium content of the carrier, but also the subsurface sodium content and sodium content in the binding layer.

The treatment of the present disclosure includes contacting a carrier with water. In one embodiment of the present disclosure, the water that is used in this contact step has a temperature from 20° C. to 100° C. In another embodiment, the water employed in this contact step has a temperature from 50° C. to 95° C. In yet another embodiment, the water employed in this contact step is from 70° C. to 90° C. The temperature of the water during the various stages of contacting can be the same or different. The contact step can also be referred to herein as a rinsing step since water is the only material used during the treatment step. The water that is employed is deionized or distilled water.

In one embodiment of the present disclosure, the carrier is treated in successive rinsing cycles, in a batch mode. The ratio of water to carrier employed in this procedure is from 1:1 to 20:1. In another embodiment of the present disclosure, the ratio of water to carrier employed in the aforementioned contacting is from 1.5:1 to 5:1. In yet another embodiment of the present disclosure, the ratio of water to carrier employed in the contacting is 2:1.

In the batch mode, water is added and circulated around a carrier for a period of time and thereafter the resultant rinse solution is recovered and analyzed for sodium. In one embodiment, the period of time in which the water circulates around the carrier is from 5 minutes to 60 minutes. In another embodiment, the period of time in which the water circulates around the carrier is from 10 minutes to 40 minutes.

In other embodiments, a continuous mode is employed. In the continuous mode, water is trickled through a column containing a bed of a carrier at a flow rate which is sufficient to thoroughly wet the bed of the carrier at all times. In the continuous mode, the rinse solution exiting the column is continuously recovered and analyzed for sodium.

In either mode mentioned above, the recovered rinse solution is analyzed for sodium content. In the batch mode, the analysis for sodium occurs after each successive rinsing step. In the continuous mode, the analysis for sodium occurs continuously.

In one embodiment, the sodium content in the rinse solution is determined, for example, by measuring the electric conductivity thereof using any suitable electrical conductivity meter. For example, the electrical conductivity of the rinse solution can be performed using an Orion 3 Star Conductivity Bench-top Meter, provided with Orion Conductivity Cell # 013005MD, Electrode (manufactured by Thermo Electron Corporation). In another embodiment, any other analytic method which can measure a sodium ion content in a rinsing solution can be used in the present disclosure.

As mentioned above, deionized water itself is not an efficient medium for electrical conductivity. Sodium ions in the deionized water will carry a current and provide a measurable electrical conductivity. The magnitude of this conductivity will be a function of the concentration of sodium that has been leached from the carrier.

The contacting, recovering and analysis for sodium is repeated any number of times until a steady state in the sodium content is achieved. The term "steady state" is defined when three, or more, successive rinsing cycles result in removing the same level of sodium, as measured by any of the aforementioned methods. In one embodiment, the steady state is achieved after 4-25 successive rinsing cycles. In another, the steady state is achieved after 5-15 successive rinsing cycles. In a further embodiment, the steady state is achieved after 5-10 successive rinsing cycles. By "same level" is meant that the electrical conductivity of the three, or more successive rinsing cycles is within a value of ±0.5%.

In another embodiment of the present invention, the steady state can be determined when the slope of the change in conductivity of the rinsing water is lower than 2µ Siemens/hour of treatment, preferably lower than 1µ Siemens per hour of rinsing, and most preferably lower than 0.5µ Siemens/hr of rinsing.

After the aforementioned treatment, the concentration of sodium at the surface of the carrier, which has achieved a steady state sodium content, is 20 ppm or less. In another embodiment of the present disclosure and after performing the above treatment, the concentration of sodium at the surface of the carrier, which has achieved a steady state sodium content, is from 5 ppm to 15 ppm. The surface sodium is measured using the water leachable test mentioned above.

The carrier that is treated by the aforementioned treatment process has a lower amount of surface sodium as compared to the same carrier prior to the treatment. In some embodiments, the reduction in surface sodium content is 25% or greater. In another embodiments, the reduction in sodium content is 50% or greater.

After reaching a steady state in sodium content, the treated carrier is dried. In one embodiment, the treated carrier is dried in oven. In another embodiment, the treated carrier is dried on a moving belt. In either embodiment, drying may be performed at a single temperature or various ramp and soak cycles can be used to dry the treated carrier. In one embodiment, the treated carrier is dried at a temperature within a range from 100° C. to 300° C. In another embodiment, the treated carrier is dried at a temperature within a range from 120° C. to 200° C. The duration of the drying may vary depending on the amount of carrier being dried, and the conditions of the drying itself. In one embodiment, the duration of the drying step can be from 1 hour to 24 hours. Other times that are above and/or below the aforementioned range can also be used in drying the carrier.

In one embodiment, an ethylene epoxidation catalyst is produced from the treated carrier described above. In order to produce the catalyst, a treated carrier having the above characteristics is then provided with a catalytically effective amount of silver thereon and/or therein. The catalysts are prepared by impregnating the treated carriers with silver ions, compounds, complexes, and/or salts dissolved in a suitable solvent sufficient to cause deposition of silver precursor compound onto and/or into the carrier. The treated carrier can be impregnated with silver, along with any desired promoters, by any of the conventional methods known in the art, e.g., by excess solution impregnation, incipient wetness impregnation, spray coating, and the like. Typically, the carrier material is placed in contact with a silver-containing solution until a sufficient amount of the solution is absorbed by the carrier. Infusion of the silver-containing solution into the carrier can be aided by application of a vacuum. A single impregnation or a series of impregnations, with or without intermediate drying, may be used, depending in part on the concentration of the silver component in the solution. Impregnation procedures are described in, for example, U.S. Pat. Nos. 4,761,394, 4,766,105, 4,908,343, 5,057,481, 5,187,140, 5,102,848, 5,011,807, 5,099,041 and 5,407,888, all of which are incorporated herein by reference. Known procedures for pre-deposition, co-deposition, and post-deposition of the various promoters can also be employed.

Silver compounds useful for impregnation include, for example, silver oxalate, silver nitrate, silver oxide, silver carbonate, silver carboxylate, silver citrate, silver phthalate, silver lactate, silver propionate, silver butyrate and higher fatty acid salts and combinations thereof. The silver solution used to impregnate the treated carrier can contain any suitable solvent. The solvent can be, for example, water-based, organic-based, or a combination thereof. The solvent can have any suitable degree of polarity, including highly polar, moderately polar or non-polar, or substantially or completely non-polar. The solvent typically has sufficient solvating power to solubilize the solution components. A wide variety of complexing or solubilizing agents may be employed to solubilize silver to the desired concentration in the impregnating medium. Useful complexing or solubilizing agents include amines, ammonia, lactic acid and combinations thereof. For example, the amine can be an alkylene diamine having from 1 to 5 carbon atoms. In one embodiment, the solution comprises an aqueous solution of silver oxalate and ethylene diamine. In some embodiments, the complexing/solubilizing agent may be present in the impregnating solution in an amount from 0.1 to 10 moles of ethylene diamine per mole of silver. In other embodiments, the complexing/solubilizing agent may be present in the impregnating solution in an amount from 0.5 to 5 moles of ethylene diamine per mole of silver. In yet a further embodiment, the complexing/solubilizing agent may be present in the impregnating solution in an amount from 1 to 4 moles of ethylene diamine per mole of silver.

In one embodiment, the concentration of silver salt in the solution is in the range from 0.1% by weight to the maximum permitted by the solubility of the particular silver salt in the solubilizing agent employed. In another embodiment, the concentration of silver salt is from 0.5% to 45% by weight of silver. In yet another embodiment, the concentration of silver salt is typically, from 5% to 35% by weight of silver.

Any one or more promoting species in a promoting amount can be incorporated into the treated carrier either prior to, coincidentally with, or subsequent to the deposition of the silver. As used herein, a "promoting amount" of a certain component refers to an amount of that component that works effectively to provide an improvement in one or more of the catalytic properties of a subsequently formed catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement is exhibited in the activity rather than in the selectivity.

For example, catalysts that are based on the treated carrier described above may include a promoting amount of an alkali metal or a mixture of two or more alkali metals. Suitable alkali metal promoters include, for example, lithium, sodium, potassium, rubidium, cesium or combinations thereof. In one embodiment, cesium can be employed. In another embodiment, combinations of cesium with other alkali metals can be employed. The amount of alkali metal will typically range from 10 ppm to 3000 ppm, more typically from 15 ppm to 2000 ppm, more typically from 20 ppm to 1500 ppm, and even more typically from 50 ppm to 1000 ppm by weight of the total catalyst, expressed in terms of the alkali metal.

The catalyst that is based on treated carrier described above may also include a promoting amount of a Group IIA alkaline earth metal or a mixture of two or more Group IIA alkaline earth metals. Suitable alkaline earth metal promoters include, for example, beryllium, magnesium, calcium, strontium, and barium or combinations thereof. The amounts of alkaline earth metal promoters are used in similar amounts as the alkali metal promoters described above.

The catalyst that is based on the treated carrier described above may also include a promoting amount of a main group element or a mixture of two or more main group elements. Suitable main group elements include any of the elements in Groups IIIA (boron group) to VIIA (halogen group) of the Periodic Table of the Elements. For example, the treated carrier can include a promoting amount of one or more sulfur compounds, one or more phosphorus compounds, one or more boron compounds, one or more halogen-containing compounds, or combinations thereof. The treated carrier can also include a main group element, aside from the halogens, in its elemental form.

The catalyst that is based on the treated carrier described above may also include a promoting amount of a transition metal or a mixture of two or more transition metals. Suitable transition metals can include, for example, the elements from Groups IIIB (scandium group), IVB (titanium group), VB (vanadium group), VIB (chromium group), VIIB (manganese group), VIIIB (iron, cobalt, nickel groups), IB (copper group), and IIB (zinc group) of the Periodic Table of the Elements, as well as combinations thereof. More typically, the transition metal is an early transition metal, i.e., from Groups IIIB, IVB, VB or VIB, such as, for example, hafnium, yttrium, molybdenum, tungsten, rhenium, chromium, titanium, zirconium, vanadium, tantalum, niobium, or a combination thereof.

In one embodiment, the one or more promoters comprise one or more species selected from Cs, K, or Li. In another embodiment, the promoter includes Re and one or more species selected from Cs, K, Li, W, and S. In a further embodiment, the promoter includes Re and one or more species selected from Cs, Li, and S.

The catalyst that is based on the treated carrier described above may also include a promoting amount of a rare earth metal or a mixture of two or more rare earth metals. The rare earth metals include any of the elements having an atomic number of 57-103. Some examples of these elements include lanthanum (La), cerium (Ce), and samarium (Sm).

The transition metal or rare earth metal promoters are typically present in an amount of from 0.1 micromoles per gram to 10 micromoles per gram, more typically from 0.2 micromoles per gram to 5 micromoles per gram, and even more typically from 0.5 micromoles per gram to 4 micromoles per gram of total catalyst, expressed in terms of the metal.

All of these promoters, aside from the alkali metals, can be in any suitable form, including, for example, as zerovalent metals or higher valent metal ions.

After impregnation with silver and any promoters, the impregnated carrier is removed from the solution and calcined for a time sufficient to reduce the silver component to metallic silver and to remove volatile decomposition products from the silver-containing support. The calcination is typically accomplished by heating the impregnated carrier, preferably at a gradual rate, to a temperature in a range of 200° C. to 600° C., more typically from 200° C. to 500° C., more typically from 250° C. to 500° C., and more typically from 200° C. or 300° C. to 450° C., at a reaction pressure in a range from 0.5 to 3 bar. In general, the higher the temperature, the shorter the required calcination period. A wide range of heating periods have been described in the art for the thermal treatment of impregnated supports. See, for example, U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose.

During calcination, the impregnated carrier is typically exposed to a gas atmosphere comprising air or an inert gas, such as nitrogen. The inert gas may also include a reducing agent.

The impregnated catalysts described above can be used for the vapor phase production of ethylene oxide by conversion of ethylene to ethylene oxide in the presence of oxygen. Generally, the ethylene oxide production process is conducted by continuously contacting an oxygen-containing gas with ethylene in the presence of the catalyst at a temperature in the range from 180° C. to 330° C., more typically from 200° C. to 325° C., and more typically from 225° C. to 270° C., at a pressure which may vary from about atmospheric pressure to 30 atmospheres depending on the mass velocity and productivity desired. A typical process for the oxidation of ethylene to ethylene oxide comprises the vapor phase oxidation of ethylene with molecular oxygen in the presence of the catalyst of the present disclosure in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

The catalysts containing the impregnated carrier described above have been shown to be particularly selective catalysts in the oxidation of ethylene with molecular oxygen to ethylene oxide. Selectivity values of at least 83 mol % up to 93 mol % are typically achieved. In some embodiments, the selectivity is from 87 mol % to 93 mole %. The conditions for carrying out such an oxidation reaction in the presence of the catalyst of the present disclosure broadly comprise those described in the prior art. This applies, for example, to suitable temperatures, pressures, residence times, diluent materials (e.g., nitrogen, carbon dioxide, steam, argon, and methane), the presence or absence of moderating agents to control the catalytic action (e.g., 1,2-dichloroethane, vinyl chloride or ethyl chloride), the desirability of employing recycle operations or applying successive conversion in different reactors to increase the yields of ethylene oxide, and any other special conditions which may be selected in processes for preparing ethylene oxide.

In the production of ethylene oxide, reactant feed mixtures typically contain from 0.5 to 45% ethylene and from 3 to 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or by-products, unreacted materials are typically returned to the oxidation reactor. For purposes of illustration only, the following are conditions that are often used in current commercial ethylene oxide reactor units: a gas hourly space velocity (GHSV) of 1500-10,000 h$^{-1}$, a reactor inlet pressure of 150-400 psig, a coolant temperature of 180-315° C., an oxygen conversion level of 10-60%, and an EO production (work rate) of 100-350 kg EO per cubic meters of catalyst per hour. More typically, the feed composition at the reactor inlet comprises 1-40% ethylene, 3-12% oxygen, 0.3-40% $CO_2$, 0-3% ethane, 0.3-20 ppmv total concentration of organic chloride moderator, and the balance of the feed comprised of argon, methane, nitrogen, or mixtures thereof.

In other embodiments, the process of ethylene oxide production includes the addition of oxidizing gases to the feed to increase the efficiency of the process. For example, U.S. Pat. No. 5,112,795 discloses the addition of 5 ppm of nitric oxide to a gas feed having the following general composition: 8 volume % oxygen, 30 volume % ethylene, about 5 ppmw ethyl chloride, and the balance nitrogen.

The resulting ethylene oxide is separated and recovered from the reaction products using methods known in the art. The ethylene oxide process may include a gas recycle process wherein a portion or substantially all of the reactor effluent is readmitted to the reactor inlet after substantially removing the ethylene oxide product and byproducts. In the recycle mode, carbon dioxide concentrations in the gas inlet to the reactor may be, for example, from 0.3 to 6, preferably from 0.3 to 2.0, volume percent.

The following non-limiting examples serve to illustrate some aspects of the present disclosure. In these examples, a Method 1 or Method 2 treatment, as described in greater detail herein below, was performed. The residual sodium content of the carrier before and after performing the treatment was determined utilizing a water leachable test. In this test, the carrier was boiled in deionized water for about 30 minutes. The ratio of water to carrier was 10:1 by weight. At the end of boiling process, the water was analyzed by Inductive Coupled Plasma (ICP).

Method 1 (Batch Mode): Hot water, 80° C., was added to an alpha-alumina carrier at a ratio of 2:1. The water was circulated around the carrier for 25 minutes and then drained for analysis. The electric conductivity of the drained water was measured at room temperature using Orion 3 Star Conductivity Bench-top Meter, provided with Orion Conductivity Cell # 013005MD, Electrode (manufactured by Thermo Electron Corporation).

An equal amount of fresh hot water was then added to the wet carrier and the process was repeated for an additional rinsing cycle. The process of draining the used water and adding a fresh replacement was repeated until a steady state is reached.

The carrier was then dried in an oven at 150° C. for three hours.

Method 2 (Continuous Mode): The carrier was placed in a cylindrical vessel and hot de-ionized water, 90° C., trickled through the cylinder at a flow rate that was necessary for the carrier bed to be thoroughly wetted at all times. The drained water was continuously analyzed for sodium content, via an electrical conductivity meter as described above in Method 1.

EXAMPLE 1

Carrier A was treated using the batch mode, Method 1, in preparation for its use as a support for an ethylene oxide catalyst. Carrier A was an α-alumina carrier that had a surface area of 0.8 m$^2$/g and its water leachable Na was 60 ppm.

TABLE 1

| Cycle # | Conductivity of drained water |
| --- | --- |
| 1 | 34.5 |
| 2 | 20.26 |
| 3 | 15.33 |
| 4 | 11.61 |

TABLE 1-continued

| Cycle # | Conductivity of drained water |
|---|---|
| 5 | 11.57 |
| 6 | 9.53 |
| 7 | 8.72 |
| 8 | 9.07 |

The treatment was considered complete because the last three conductivity readings indicated that a steady state was reached. The carrier was then dried and its water leachable Na was 10 ppm.

EXAMPLE 2

Carrier B was treated using Method 1, in preparation for its use as a support for an ethylene oxide catalyst. Carrier B was an α-alumina carrier that had a surface area of 0.7 m$^2$/g and its water leachable Na was 72 ppm.

TABLE 2

| Cycle # | Conductivity of drained water |
|---|---|
| 1 | 112.4 |
| 2 | 52.4 |
| 3 | 36.3 |
| 4 | 30.2 |
| 5 | 22 |
| 6 | 21.04 |
| 7 | 18.79 |
| 8 | 18.45 |
| 9 | 14.2 |
| 10 | 13.2 |
| 11 | 12.7 |
| 12 | 12.4 |
| 13 | 12.5 |

The treatment was considered complete because the last three conductivity readings indicated that a steady state was reached. The carrier was then dried and its water leachable Na was 14 ppm.

EXAMPLE 3

Carrier C was treated using the continuous mode, Method 2, in preparation for its use as a support for an ethylene oxide catalyst. Carrier C was an α-alumina carrier that had a surface area of 0.7 m$^2$/g and its water leachable Na was 26 ppm. The carrier amount used was 130 Kg and throughout the entire procedure the 90° C. water flow rate was adjusted at 3 gallon/min. The conductivity of the rinsing water was measured immediately as it exited the treatment vessel.

The details of the procedure are illustrated in Table 3 and the data from the table are shown in FIGS. 1 and 2.

TABLE 3

| Rinsing time min | Conductivity μS | Slope of decline in conductivity μS/min | Slope of decline in conductivity μS/hour |
|---|---|---|---|
| 0 | 15.3 | 0.08 | 4.8 |
| 10 | 12.1 | | |
| 20 | 11.3 | | |
| 30 | 10.2 | | |
| 40 | 9.1 | | |
| 50 | 8.4 | 0.029 | 1.74 |
| 60 | 7.9 | | |
| 70 | 7.5 | | |
| 80 | 7.1 | | |
| 90 | 6.8 | | |
| 100 | 6.5 | | |
| 110 | 6.1 | | |
| 120 | 5.8 | | |
| 130 | 5.8 | | |
| 140 | 5.6 | | |
| 150 | 5.7 | | |
| 160 | 5.5 | 0.0193 | 1.16 |
| 170 | 5.3 | | |
| 180 | 5.1 | | |
| 190 | 5 | | |
| 210 | 4.9 | | |
| 220 | 4.9 | | |
| 230 | 4.8 | | |
| 240 | 4.7 | | |
| 250 | 4.6 | | |
| 260 | 4.5 | | |
| 270 | 4.4 | 0.01 | 0.6 |
| 280 | 4.3 | | |
| 290 | 4.3 | | |
| 300 | 4.2 | | |
| 310 | 4.2 | 0.005 | 0.3 |
| 320 | 4.2 | | |
| 330 | 4.1 | | |

The treatment was considered complete because the slope of the change in conductivity of the rinsing water is lower than 0.5μ Siemens/hr. This indicated that a steady state was reached. The carrier was then dried and its water leachable Na was 12 ppm.

EXAMPLE 4

Carrier C was treated using the continuous mode, Method 2, in preparation for its use as a support for an ethylene oxide catalyst. The carrier amount used was 134 Kg and the throughout the entire procedure the 90° C. water flow rate was adjusted at 6 gallon/min. The conductivity of the rinsing water was measured immediately as it exited the treatment vessel. The details of the procedure are illustrated in Table 4 and the data from the table are shown FIGS. 3 and 4.

TABLE 4

| Rinsing time Min | Conductivity μS | Slope of decline in conductivity μS/min | Slope of decline in conductivity μS/hour |
|---|---|---|---|
| 0 | 15.3 | 0.1 | 6 |
| 10 | 12.1 | | |
| 20 | 11.3 | | |
| 30 | 10.2 | | |
| 40 | 9.1 | | |
| 50 | 8.4 | 0.04 | 2.4 |
| 60 | 7.9 | | |
| 70 | 7.5 | | |
| 80 | 7.1 | | |
| 90 | 6.8 | | |
| 100 | 6.5 | 0.015 | 0.9 |
| 110 | 6.1 | | |
| 120 | 5.8 | | |
| 130 | 5.8 | | |
| 140 | 5.6 | | |
| 150 | 5.7 | | |
| 160 | 5.5 | 0.0119 | 0.7 |
| 170 | 5.3 | | |
| 180 | 5.1 | | |
| 190 | 5 | | |
| 210 | 4.9 | | |
| 220 | 4.9 | 0.01 | 0.6 |
| 230 | 4.8 | | |

TABLE 4-continued

| Rinsing time Min | Conductivity μS | Slope of decline in conductivity μS/min | Slope of decline in conductivity μS/hour |
|---|---|---|---|
| 240 | 4.7 | | |
| 250 | 4.6 | | |
| 260 | 4.5 | | |
| 270 | 4.4 | | |
| 280 | 4.3 | | |
| 290 | 4.3 | 0.004 | 0.24 |
| 300 | 4.2 | | |
| 310 | 4.2 | | |
| 320 | 4.2 | | |
| 330 | 4.1 | | |

The treatment was considered complete because the slope of the change in conductivity of the rinsing water is lower than 0.5μ Siemens/hr. This indicated that a steady state was reached. The carrier was then dried and its water leachable Na was 11 ppm.

EXAMPLE 5

Stock Solution for Catalyst A: An 834 g portion of high purity silver oxide (Ames Goldsmith Corp.) was added to a stirred solution of 442 g oxalic acid dehydrate (ACS Certified Reagent, Fisher) in about 2,800 g deionized water. A precipitate of hydrated silver oxalate salt formed on mixing. Stirring was continued for 0.5 hours. The precipitate was then collected on a filter and washed with deionized water. Analysis showed that the precipitate contained 50.5 wt % silver. Next, 213.9 g of the silver oxalate precipitate was dissolved in a mixture of 77.2 grams ethylenediamine (99+ %, Aldrich) and 60.3 g deionized water. The temperature of the solution was kept below 40° C. by combining the reagents slowly, and by cooling the solution. After filtration, the solution contained roughly 30 wt % silver, and had a specific gravity of 1.52 g/mL.

Carrier for Catalyst A: For this catalyst, the carrier that was used, Carrier A, was treated in accordance with Example 1 of the present disclosure. Analysis of the treated carrier showed that the residual sodium value was 10 ppm.

Catalyst A Preparation

Silver based catalyst preparation and activation followed generally conventional procedures, as disclosed above. Specifically, a 300 g portion of the alumina support was placed in a flask and evacuated to about 0.1 ton prior to impregnation. To the above silver solution were added aqueous solutions of cesium hydroxide, perrhenic acid, and ammonium sulfate in order to prepare a catalyst composition according to examples 5-10 of U.S. Pat. No. 4,766,105 to Lauritzen et al. After thorough mixing, the promoted silver solution was aspirated into the evacuated flask to cover the carrier while maintaining the pressure at about 0.1 torr. The vacuum was released after about 5 minutes to restore ambient pressure, hastening complete penetration of the solution into the pores. Subsequently, the excess impregnation solution was drained from the impregnated carrier.

Calcination of the wet catalyst was performed on a moving belt calciner. In this unit, the wet catalyst was transported on a stainless steel belt through a multi-zone furnace. All zones of the furnace were continuously purged with pre-heated, nitrogen and the temperature was increased gradually as the catalyst passed from one zone to the next. The heat supplied to the catalyst was radiated from the furnace walls and from the preheated nitrogen. In this example, the wet catalyst entered the furnace at ambient temperature. The temperature was then increased gradually to a maximum of about 450° C. as the catalyst passed through the heated zones. In the last (cooling) zone, the temperature of the now calcined catalyst was immediately lowered to less than 100° C. before it emerged into ambient atmosphere. The total residence time in the furnace was approximately 45 minutes.

Catalyst B, a high selectivity catalyst was prepared using the same carrier and same impregnating solution as used in catalyst A. The only exception is that the carrier was washed using a limited washing protocol such as typically employed in the prior art in which a steady-state conductivity was not meant. Analysis of the treated carrier showed that the residual sodium value was 26 ppm.

The two catalysts were tested under stressful conditions of work rate and gas composition in order to accelerate their ageing. The decline in selectivity of the two catalysts demonstrate that the catalyst that was prepared using a carrier as treated using the method of the present disclosure is more stable. This is shown, for example, in the FIG. 5.

While the present disclosure has been particularly shown and described with respect to various embodiments thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

What is claimed is:

1. A carrier for a silver-based ethylene oxide catalyst, said carrier having a steady state sodium content of from 5 ppm to 15 ppm.

2. The carrier of claim 1, wherein said carrier comprises an alumina carrier comprising 80 weight percent or more alpha-alumina.

3. The carrier of claim 2, wherein said alumina carrier further comprises other phases of alumina, silica, mullite, or alkali metal oxides.

4. The carrier of claim 2, wherein said alumina carrier has a B.E.T. surface area from 0.2 $m^2$/g to 3 $m^2$/gm.

5. The carrier of claim 4, wherein said alumina carrier has a water absorption from 0.22 cc to 0.8 cc/g.

6. The carrier of claim 2, wherein said alumina carrier has a monodal pore size distribution comprising pores having a pore diameter of at least 0.01 microns.

7. The carrier of claim 2, wherein said alumina carrier has a multimodal pore size distribution in which at least 40 percent of the pore volume is attributed to pores with diameters between 1 micrometer and 5 micrometers.

8. The carrier of claim 2, wherein said alumina carrier has a pore volume from pores with a diameter of 1 micrometer and less of less than 0.20 ml/g, and a pore volume from pores with a diameter of 5 micrometers and above of less than 0.20 ml/g.

9. The carrier of claim 1, further comprising a catalytic effective amount of silver, and a promoting amount of at least one promoter disposed on said carrier.

10. A silver-based ethylene oxide catalyst comprising:
   a carrier having a steady state sodium content of from 5 ppm to 15 ppm;
   a catalytic effective amount of silver; and
   a promoting amount of at least one promoter.

11. The silver-based ethylene oxide catalyst of claim 10, wherein said carrier comprises an alumina carrier comprising 80 weight percent or more alpha-alumina.

12. The silver-based ethylene oxide catalyst of claim 10, wherein said catalytic effective amount of silver is from 0.5 to 45 percent by weight silver.

13. The silver-based ethylene oxide catalyst of claim 10, wherein said at least one promoter comprises an alkali metal, a Group IIA alkaline earth metal, a main group element from Group IIA to VIIA of the Periodic Table of Elements, or a transition metal from Group IIIB, IVB, VB, VIB, VIIB, VIIIB, IB and IIB of the Periodic Table of Elements.

14. The silver-based ethylene oxide catalyst of claim 10, wherein said at least one promoter is selected from one or more of Cs, K and L.

15. The silver-based ethylene oxide catalyst of claim 10, wherein said at least one promoter comprises Re.

16. The silver-based ethylene oxide catalyst of claim 15, wherein said at least one promoter further comprises one or more of Cs, K, Li, W and S.

17. The silver-based ethylene oxide catalyst of claim 15, wherein said at least one promoter further comprises one or more of Cs, Li and S.

\* \* \* \* \*